United States Patent [19]

Degen et al.

[11] 4,115,547

[45] Sep. 19, 1978

[54] SUNSCREENING COMPOSITIONS

[75] Inventors: Peter John Degen, Woodbury Township, Washington County; Anthony James Lucas, Oakdale, both of Minn.

[73] Assignee: Minnesota Mining and Manufacturing Company, Saint Paul, Minn.

[21] Appl. No.: 734,036

[22] Filed: Oct. 20, 1976

Related U.S. Application Data

[62] Division of Ser. No. 492,180, Jul. 26, 1974, Pat. No. 4,002,733.

[51] Int. Cl.² ................................................ A61K 7/44
[52] U.S. Cl. ........................................ 424/60; 424/59; 260/302 F
[58] Field of Search ..................................... 424/59, 60

[56] References Cited

U.S. PATENT DOCUMENTS

| 3,366,668 | 1/1963 | Strobel et al. | 260/475 |
| 3,506,758 | 4/1970 | Epstein et al. | 424/60 |
| 3,708,435 | 1/1973 | Starkman | 424/358 X |
| 3,799,969 | 3/1974 | Hoppe | 424/60 |

FOREIGN PATENT DOCUMENTS

| 641,570 | 2/1937 | Fed. Rep. of Germany | 424/59 |
| 2,009,600 | 9/1971 | Fed. Rep. of Germany | 424/59 |
| 7,114,005 | 4/1973 | Netherlands | 424/59 |

OTHER PUBLICATIONS

Chemical Abstracts, 1970, vol. 72, p. 98976.

*Primary Examiner*—Dale R. Ore
*Attorney, Agent, or Firm*—Cruzan Alexander; Donald M. Sell; Carolyn A. Bates

[57] ABSTRACT

Sunscreening compositions are disclosed which comprise a pharmaceutical extending medium having incorporated therein a substantive, dermally non-irritating, ultraviolet light absorbing compound which is a polyfunctional organic molecule containing two or more ultraviolet absorbing moieties connected by two or more polar linking groups to one or more aliphatic bridging groups. These sunscreening compositions are resistant to removal by water and mild abrasion but are readily removed by soap and water.

6 Claims, No Drawings

SUNSCREENING COMPOSITIONS

This is a division of application Ser. No. 492,180 filed July 26, 1974, now U.S. Pat. No. 4,002,733.

This invention relates to sun-screening compositions which are substantive to skin and useful in protecting the skin against erythema-producing radiation. A further aspect of the invention relates to novel ultraviolet light-absorbing compounds which comprise the preferred sun-screening compositions of the invention.

It is well-known that human skin is sensitive to sunlight and artificial light containing radiation or wavelengths between about 290 nanometers (nm) and 360 nm. Radiation between 290 nm and 330 nm is known to produce the most damaging effects on the skin. These damaging effects include reddening or erythema; edema, blistering and other skin eruptions in more severe cases. Prolonged or chronic exposure to radiation in this wavelength range has been associated with serious skin conditions such as actinic keratoses and carcinomas of the skin.

To protect skin against erythema-producing radiation, a number of so-called "sun-screening" agents have been developed which can be applied to the skin in order to absorb a large amount of the harmful radiation before it reaches the skin. Commonly-known ultraviolet-absorbing compounds for use as sun-screening agents include P-aminobenzoic acid and its ester derivatives, cinnamic acid and certain derivatives thereof and salicylic acid and certain of its ester derivatives.

While the above compounds are generally effective ultraviolet light absorbers, their practical usefulness as sun-screening agents is less than adequate for one or more reasons. The primary disadvantage of these known ultraviolet-absorbers is their lack of substantivity to skin which results in their ready removal by contact with water. Repeated applications of these materials are therefore necessary in order to insure adequate protection against sunburning. Other disadvantages of some of these compounds include instability upon storage or exposure to light and discoloration of fabrics.

Attempts have been made to chemically modify known ultraviolet-absorbing compounds to increase their overall desirability as sun-screening agents. For example, U.S. Pat. No. 3,403,207 describes the esterification of p-dimethyl-aminobenzoic acid with certain alcohols having at least five carbon atoms such as amyl, hexyl, octyl, etc. U.S. Pat. No. 3,574,825 describes polymethylated, muconic acids and hydrocarbyl mono- and di-esters thereof containing hydrocarbyl groups with from one to twenty carbon atoms.

The esterification of the ultraviolet-absorbing compounds, P-aminobenzoic acid and salicylic acid with lecithins and/or choline and/or imidazoles is disclosed in U.S. Pat. No. 3,506,758. The esters are further reacted to product quaternary salts which are described as being substantive to skin.

While the above-cited patents described relatively low-molecular weight derivatives of certain known ultraviolet absorbing molecules, polymeric derivatives of known ultraviolet-absorbers have also been described. U.S. Pat. No. 3,795,733 describes certain ethylenically-unsaturated derivatives of P-aminobenzoic acid prepared by reaction with allyl chloride. These monomers are co-polymerized with a variety of conventional vinyl monomers to provide water-insoluble, soap-removable, long-lasting sun-screening agents. U.S. Pat. No. 3,493,539 describes similar polymeric sun-screening agents preapred by the polymerization of monomeric derivatives of 2-(2-hydroxyphenyl) benzotriazole with conventional vinyl monomers.

The polymerization of ethylenically unsaturated derivatives of ultraviolet-absorbing compounds with acidic comonomers comprising ethylenically-unsaturated carboxylic acids containing at least one available carboxylic group is described in U.S. Pat. No. 3,529,055.

The polymeric sun-screening agents described in the above-cited patents are characterized as high-molecular weight polymers having an aliphatic polymeric backbone with pendant ultraviolet-absorbing moieties and pendant polar groups. The functional moieties themselves do not form part of the polymeric backbone.

Prior modifications of known ultraviolet-absorbing compounds have resulted in a number of sun-screening agents which achieve a degree of substantivity to skin. However, none have achieved a high degree of substantivity combined with other desirable physical and chemical properties such as ease of preparation, low-cost production, ease of formulation into appealing topical preparations and ease of removal with soap and water.

The sunscreening compositions of the present invention successfully overcome the deficiencies of prior art sun-screening agents by providing compositions which effectively absorb ultraviolet radiation in the erythemal range while remaining strongly adhered to the skin even in the presence of severe challenges by fresh and salt water. The sun-screening compositions of the present invention are surprisingly removable with soap and water during the normal act of bathing. In addition, sunscreening compositions of the present invention are easily and economically prepared and are cosmetically-appealing to the touch.

Accordingly, the present invention provides sun-screening compositions for application to the skin comprising a pharmaceutical extending media having incorporated therein an active sunscreening agent. These sunscreening agents are substantive, dermally non-irritating polyfunctional organic molecules containing two or more ultraviolet-absorbing moieties connected by two or more polar linking groups to one or more aliphatic hydrocarbon bridging group(s). The substantive, dermally non-irritating, sunscreening agents of the composition are defined by the following formula: Formula 1:

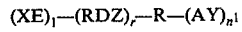

Wherein R is a saturated or unsaturated aliphatic or cycloaliphatic radical containing 8 to 108 carbon atoms; A, D an E are independently

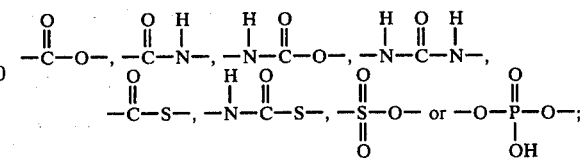

X and Z are aromatic, ultraviolet light absorbing moieties characterized by ultraviolet light absorption maxima in the range of 280 nm to about 360 nm; Y is an aromatic ultraviolet light-absorbing moiety characterized by an ultraviolet light absorption maxima in the range of 280 nm to 360 nm, and when $n + n^1$ is greater than 2, Y is hydrogen or an alkyl radical containing 1 to 6 carbon atoms; $n$ and $n^1$ are independently integers from 1 to 9 designated different or the same (XE)— and —(AY) respectively must equal 2–10; and $r$ is zero or an integer from 1 to 25. Any of the available valences on the polar linking groups A, D and E can be attached to either the R-group or the ultraviolet-absorbing groups X, Y and Z.

Compounds of Formula 1 are characterized by having ultraviolet absorption maxima (derived from the $(XE)_n$, $(DZ)_r$ and $(EY)_{n1}$ portions of the molecule) in the range of 280 to 360 nm when applied to a proteinaceous surface and by a molar extinction coefficient (Epsilon value) of at least 10,000. Moreover, each —(RDZ)— radical must contribute at least a value of 5,000 to the Epsilon value of the compound.

The term "substantive" as used herein to describe the compositions of the invention refers to the inability to remove a majority of the material from a proteinaceous surface with water or simple abrasion.

The A, D and E groups of Formula 1 are the polar linking groups of the compounds and connect the ultraviolet absorbing moieties X, Y and Z with the aliphatic hydrocarbon radical(s) R. These polar-linking groups are either ester, thioester, amide, urea, urethane, sulfonate, phosphate or thiourethane groups. The polar-linking groups are formed by the reaction of a polyfunctional, R-containing compound, having the proper functional groups, with an X, Y and Z-containing compound having the appropriate functional group to form the desired polar linking groups A, D or E between R and X, Y or Z. For example, it is obvious to one skilled in the art that reacting an acid with an alcohol will form an ester linking group; reacting an acid with an amine will form an amide linking group; reacting an isocyanate with an alcohol with form a urethane linking group and so forth.

The R-group of Formula 1 is the saturated or unsaturated, aliphatic or cycloaliphatic portion of a polyfunctional compound containing 8 to 108 carbon atoms. Examples of suitable starting materials from which the R-substituent can be derived are given in the following Table I.

TABLE I

| STARTING MATERIALS FROM WHICH THE R-FORMING SUBSTITUENT MAY BE SELECTED | |
|---|---|
| STRUCTURE | CHEMICAL NAME |
| ACIDS | |
| $HOC(=O)-(CH_2)_8-COH(=O)$ | decanedioic acid |
| $HOC(=O)-(CH_2)_{10}-COH(=O)$ | dodecandioic acid |
| $HOC(=O)-(CH_2)_{11}-COH(=O)$ | tridecanedioic acid |
| $HOC(=O)-(CH_2)_{14}-COH(=O)$ | hexadecanedioic acid |
| $HOC(=O)-(R)-COH(=O)$ | Hystrene® 3695 "Dimer Acid" (R = aliphatic portion of a dimerized $C_{18}$ fatty acid) |
| $R-(COH(=O))_n$ | Empol® 1056A Polybasic Acid" (R = aliphatic portion of polymerized $C_{18}$ fatty acid, N= tetradecylsuccinic acid |
| $HOOC-CH(C_{14}H_{29})-CH_2-COOH$ | |
| $HOOC-CH(C_{20}H_{41})-COOH$ | eicosylmalonic acid |
| $HOOC-CH(C_{14}H_{29})-COOH$ | tetradecylmalonic acid |
| $HOOC\text{-}C(=CH(CH_2)_8CH(CH_3)-(CH_2)_2CH(CH_3)-(CH_2)_6CH_3)\text{-}HOOC$ | 12,15-dimethyl-docosene (1,2)-dicarboxylic acid (1,1) |
| $HOOC-(CH_2)_6CH=CH-(CH_2)_{10}-COOH$ | eicosene (8) - dicarboxylic acid (1,20) |
| ALCOHOLS | |
| $HOH_2C-(CH_2)_8-CH_2OH$ | 1, 10-decanediol |
| $HOH_2C-(CH_2)_{10}-CH_2OH$ | 1, 12-dodecanediol |
| $HOH_2C-(CH_2)_{11}-CH_2OH$ | 1, 13-tridecanediol |
| $HOH_2C-(R)-CH_2OH$ | reduced Hystrene® 3695 (R = aliphatic portion of a dimerized $C_{18}$ fatty acid |
| $R-(CH_2OH)_n$ | reduced Empol® 1056A (R = aliphatic portion of polymerized $C_{18}$ fatty acid n = 2–6) |
| AMINES | |
| $H_2N-(CH_2)_{12}-NH_2$ | dodecane diamine |

TABLE I-continued
STARTING MATERIALS FROM WHICH THE R-FORMING SUBSTITUENT MAY BE SELECTED

| STRUCTURE | CHEMICAL NAME |
|---|---|
| 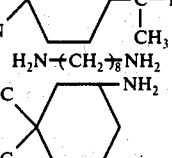 | menthane diamine |
| $H_2N{+}CH_2{\rightarrow}_8 NH_2$ | 1, 8 octane diamine |
| 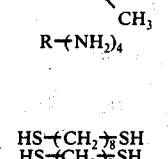 | isophorone diamine |
| $R{+}NH_2)_4$ | General Mills Brand "Modified Amine" A-100. (R = aliphatic portion of polymerized fatty acid) |
| MERCAPTANS | |
| $HS{+}CH_2{\rightarrow}_8 SH$ | 1, 8- octanedithiol |
| $HS{+}CH_2{\rightarrow}_9 SH$ | 1, 9- nonanedithiol |
| $OCN{+}CH_2{\rightarrow}_{12} NCO$ | 1, 12- diisocyanate dodecane |
| 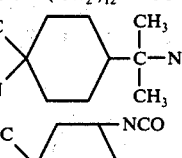 | diisocyanate menthane |
| 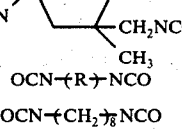 | diisocyanate isophorone |
| $OCN{+}R{\rightarrow}NCO$ | General Mills Brand DDI® -1410 (R = C$_{36}$ aliphatic radical) |
| $OCN{+}CH_2{\rightarrow}_8 NCO$ | 1, 8- diisocyanate octane |

The X, Y and Z moieties of Formula 1 are the ultraviolet absorbing or "chromophore" groups of the sunscreen agents. The coreactants which generate these moieties are aromatic ultraviolet absorbing molecules known to those skilled in the art. The coreactants are generally substituted aromatic compounds which have ultraviolet absorpotion maxima in the range of 280 nm to 360 nm. The aromatic compounds must contain at least 2 polar substituents and, at least one such polar substituent must be available for reaction with the R-containing coreactant to form the polar linking groups A, D or E. Other polar substituents are necessary to impart ultraviolet absorption having the desired wave length and intensity. Typical polar substituents which can be used to impart ultraviolet absorption in the desired range include alkoxy, aryloxy, acyl, benzoyl, acryloyl, arylsulfonyl, mercapto, oxazole, imidazole, thiazole, carboxyl, carbonamido, dialkyl amino, amino and hydroxyl substituents.

The chromophore moieties X, Y and Z are formed from known aromatic ultraviolet absorbing compounds. The particular substituents on the aromatic ring and their location on the ring are not critical to the practice of the invention so long as they provide the necessary ultraviolet absorption. The X, Y and Z moieties are not believed to measurably affect the substantive or detergent-removable properties of the compositions of the invention.

Preferred substituents on the benzene ring are those which interact by means of resonance and inductive effects to enhance the ultraviolet absorbance in the region of 280 to 360 nm. Particularly preferred are auxochromic substituents containing polar groups which bear unshared electrons and other substituents which introduce double bonds alpha to the aromatic ring which enter into resonance with the aromatic ring. These resonance interactions result in bathochromic shifts which give rise to strong ultraviolet absorption in the range of 280 nm to 360 nm. By considering the combined effect of the bathochromic properties of particular substituents and their location on the aromatic ring, it is possible to design compounds which will provide ultraviolet absorption maxima in the proper range. (See, for example, Jaffe and Orchin, *Theory and Applications of Ultraviolet Spectroscopy*; J. Wiley and Sons, New York, New York, 1962, p. 259-270.)

A considerable number of aromatic compounds containing a variety of polar substituents in various positions on the aromatic ring are suitable starting materials for generating the X, Y and Z moieties of Formula 1. The various preferred combinations of particular polar substituents and their relative positions on the aromatic ring are well known to those skilled in the art. It is known that polar substituents on the benzene ring in the 1, 2; 1, 4; and 1, 2, 4 positions (where the 1 position denotes the position occupied by A, D, and E) are especially preferred in providing chromophores with ultraviolet absorption in the range of 280 nm to 360 nm. The preferred substituents in these positions are: hydroxy and alkoxy groups containing 1 to 6 carbon atoms; amino or alkylamino containing 1 to 6 carbon atoms; thioalkyl containing 1 to 6 carbon atoms; carboxy, aromatic or aliphatic (1 to 6 carbon atoms) carboxylic esters; aryl or alkyl (1 to 6 carbon atoms) carbonamides; aryl or alkyl (1 to 6 carbon atoms) ketones; substituted or unsubstituted phenoxy; acrylyl and aliphatic (1 to 6 carbon atoms) esters; substituted or unsubstituted alkenes (1 to 6 carbon atoms); benzenesulfonyl wherein the benzene ring may bear hydroxy, alkoxy (1 to 6 carbon atoms), amino, alkylamino (1 to 6 carbon atoms) carboxyl or alkyl carboxyl (1 to 6 atoms). In addition, heterocyclic rings containing from 4 to 6 atoms fused to an aromatic nucleus exemplified by benzoxazole, benzimidazole, benzothiazole and benzotriazole are also preferred substituents on the benzene ring.

For most purposes, the X, Y and Z moieties of Formula 1 may be substituted benzene ring selected from the group consisting of

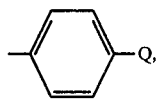
A.

where Q is (1) —CO$_2$H, —CO$_2$R$^1$, —CON(R$^1$)$_2$, —N(R$^1$)$_2$, —SR$^1$, and R$^1$ is an aliphatic or cycloaliphatic, saturated or unsaturated radical containing 1 to 10 carbon atoms;

(2)

and R$^2$ is an aliphatic or cycloaliphatic, saturated or unsaturated radical containing 1 to 10 carbon atoms optionally substituted with halogen, a saturated or unsaturated aliphatic or cycloaliphatic alkoxy radical containing 1 to 10 carbon atoms, or an amino or amine-substituted saturated or unsaturated aliphatic or cycloaliphatic radical containing 1 to 10 carbon atoms;

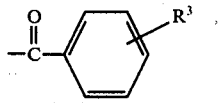
(3)

and R$^3$ is: hydrogen, an aliphatic or cycloaliphatic alkyl or alkoxy radical containing 1 to 10 carbon atoms, —OH, —F, —Cl, —CO$_2$H, or —CO$_2$R$^1$ where R$^1$ is as defined above.

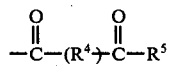
(4)

and R$^4$ is: a saturated or unsaturated, aliphatic or cycloaliphatic radical containing 1 to 10 carbon atoms optionally substituted by —OH, —CO$_2$H, —OR$^1$, —F or —Cl; and R$^5$ is —OH, —NH$_2$, —NHR$^1$, —N(R$_1$)$_2$, —OR$^1$ where R$^1$ is as defined above.

(5) —CH=CH—R$^6$ and R$^6$ is: an aliphatic or cycloaliphatic alkyl radical containing 1 to 10 carbon atoms; an aromatic nucleus which may be optionally substituted with —OH, —NH$_2$, —SH, —F, —Cl, —R$^1$ or —OR$^1$ where R$^1$ is as defined above; —COR$^7$ where R$^7$ is hydrogen or an aliphatic or cycloaliphatic alkyl radical containing 1 to 10 carbon atoms, —OH, —NH$_2$, —N(R$^8$)$_2$ or —OR$^8$ where R$^8$ is an aliphatic or cycloaliphatic, saturated or unsaturated radical containing 1 to 10 carbon atoms.

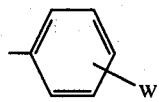
B.

where W is: benzimidazole, benzoxazole or benzothiazole and the benzo radical may optionally bear halogen, hydroxyl and/or an aliphatic or cycloaliphatic alkyl radical containing from 1 to 10 carbon atoms.

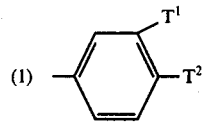
C.

where T$^1$ is: —NH$_2$, —OH, —SH, —SR$^8$, —N(R$^8$)$_2$ or —OR$^8$ where R$^8$ is as defined above; and T$^2$ is: —CO$_2$H, —CO$_2$R$^9$, —COR$^9$ or —CON(R$^9$)$_2$ where R$^9$ is an aliphatic or cycloaliphatic, saturated or unsaturated radical containing 1 to 10 carbon atoms.

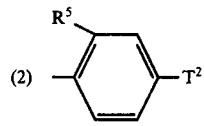

where R$^5$ and T$^2$ are as defined above.

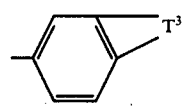
D.

where T$^3$ represents a 3 to 5 atom radical required to form a fused heterocyclic ring containing C, O, N and/or S such as imidazole, thiazole, oxazole, pyrone or a pyridine ring.

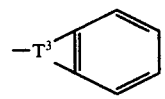
E.

where T$^3$ is as defined above.

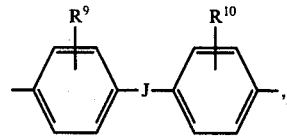
F.

where J is —$\overset{\overset{O}{\|}}{C}$—, —$\overset{\overset{S}{\|}}{C}$—, —$\overset{\overset{O}{\|}}{S}$—, —$\overset{\overset{O}{\|}}{\underset{\underset{O}{\|}}{S}}$— and R$^9$ and R$^{10}$ are hydrogen, halogen, —OH, mercapto, —OR$^8$ or —R$^8$ where R$^8$ is as defined above.

It is known to those skilled in the art that any substituent position bearing a hydrogen in the above chromophores may be substituted with a alkyl radical containing 1 to 6 carbon atoms without substantial effect on the position or intensity of the ultraviolet absorbance of the chromophore.

Typical starting materials from whith the X and Y chromophore moities of Formula 1 may be generated include:
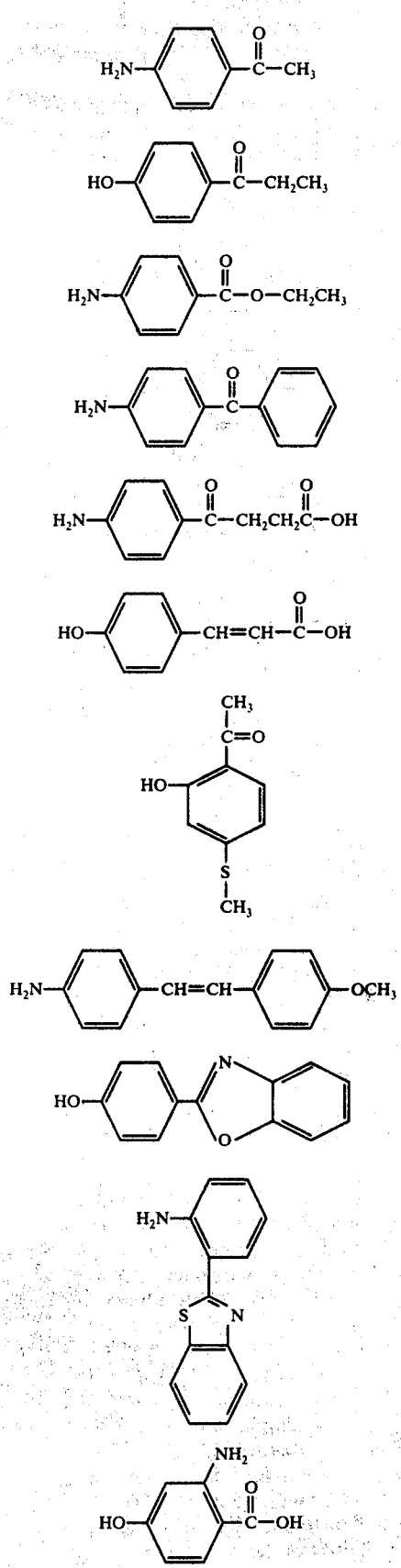
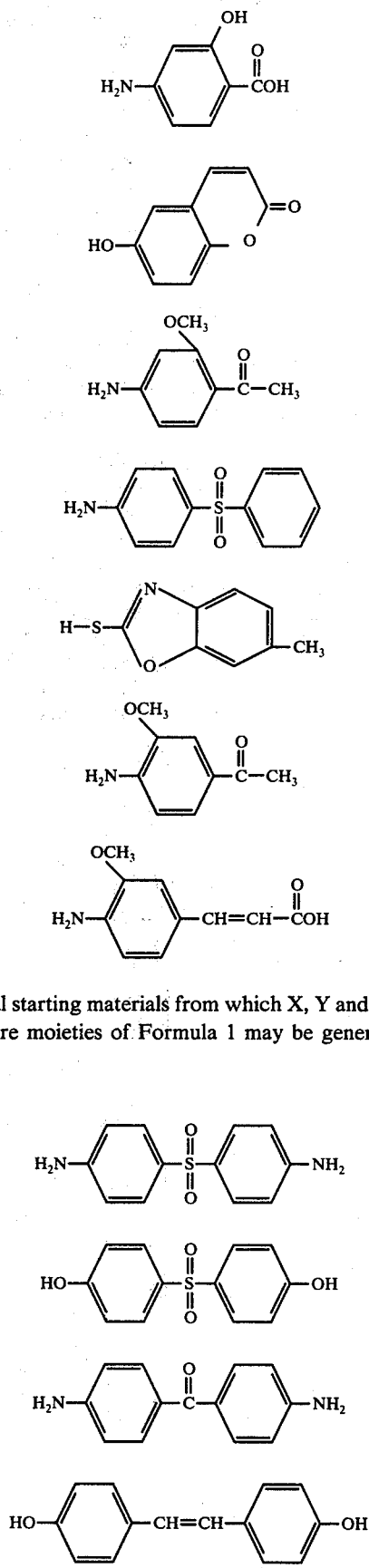
Typical starting materials from which X, Y and Z chromophore moieties of Formula 1 may be generated include:

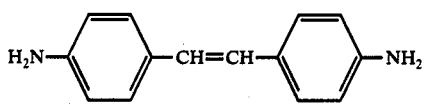

The general procedure for preparing the compounds of Formula 1 involves the condensation of a poly-functional, saturated or unsaturated, aliphatic or cycloaliphatic (R-forming) compound with functional aromatic, ultraviolet absorbing (X, Y and Z forming) compounds. The coreactants are admixed in a suitable, non-reactive solvent at from ambient temperature to the boiling point of the solvent. Suitable non-reactive solvents include acetone, 2-butanone, tetrahydrofuran, p-dioxane, benzene and toluene. The preferred range of reaction temperature is from 20° to 100° C. and the preparation of certain products may be facilitated by the presence of catalysts although their presence is not required.

Useful catalysts for preparing compounds of Formula 1 where the linking group is ester or amide include sulfuric acid p-toluenesulfonic acid and N,N'-dicyclohexylcarbodiimide. Useful catalysts for preparing compounds of Formula 1 where the linking group is urea or urethane include lead octoate, stannousoctoate, dibutytindilaureate, zincoctoate, cadmium octoate, cobaltous octoate and ferric acetylacetonate. A comprehensive discussion of catalysts useful in the latter reactions is found in K. C. Frisch and J. H. Saunders, *Polyurethanes, Chemistry and Technology*, Volume 1, Interscience New York, 1962.

The condensation reaction is generally complete within 2 to 40 hours and the reaction generally proceeds at a conversion in the range of about 75 to 100% of the coreactants. The molar ratio of the R-forming coreactant to the ultraviolet absorbing coreactants X, Y and Z may vary over the range of 2 to 0.5 respectively, with the preferred compositions being prepared by employing stoichiometric quantities of the coreactants.

A preferred group of sunscreen compositions of the invention comprises substantive, dermally non-irritating compounds of the following formula: Formula 2

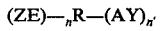

wherein R, Z and Y are as defined above in Formula 1; E and A are together or independently

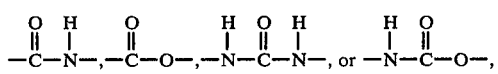

and n and n' are as defined in Formula 1; and a pharmaceutically extending medium compatable therewith.

An especially preferred group of sunscreening compositions of the invention are those comprising a pharmaceutical extending medium having incorporated therein a substantive, dermally non-irritating novel compound of the Formula: Formula 3

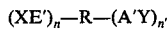

wherein R is a saturated or unsaturated aliphatic or cycloaliphatic, organic radical containing 8 to 108 carbon atoms; E' and A' are independently

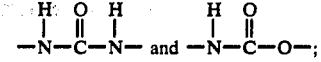

X and Y are ultraviolet absorbing aromatic radicals as defined in Formula 1; and n and n' are as defined in Formula 1.

Particularly preferred compounds of Formula 3 for use as substantive sunscreening agents are those wherein n and n' are each one and X and Y are independently

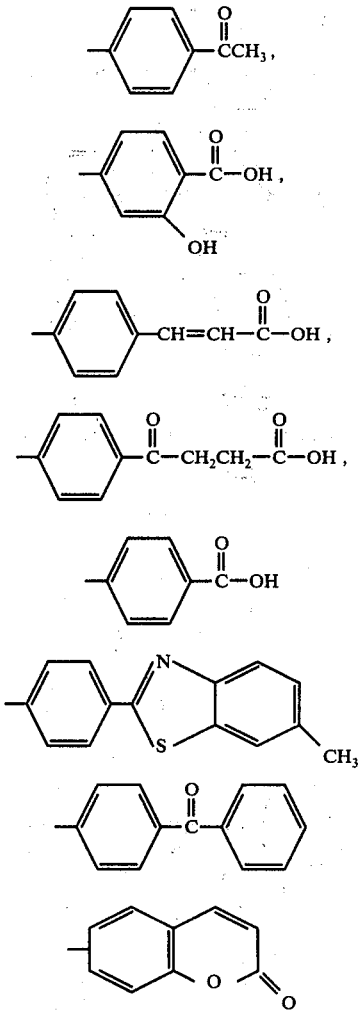

The especially preferred R-containing starting materials for preparing compounds of Formula 3 are commercially available di- and poly isocyanates, such as "dimer diisocyanate" (commercially available as General Mills Brand DDI$^R$-1410). Dimer diisocyanate is a difunctional molecule containing 36 carbon atoms and is a particularly preferred starting material. DDI diisocyanate 1410 is derived from a dimeric fatty acid. The latter is derived from controlled polymerization of 18-carbon fatty acids resulting in an aliphatic dibasic acid containing 36 carbon atoms. Higher analogues of this material can contain three, four, five and six reactive isocyanate groups and contain up to 108 carbon atoms.

The pharmaceutically acceptable extending medium which comprises the sunscreening compositions of the invention refers to a carrier or vehicle for the active sunscreening agent which adapts the sunscreening agent for application to the skin.

A variety of procedures may be employed to incorporate the substantive sunscreening agents into pharmaceutically acceptable sunscreening formulations depending upon the type of sunscreening formulation desired. It is possible to prepare such formulations in the form of organic solvent solutions, aqueous emulsions, gels or the so-called "aerosol" formulations. Of the various optional ingredients which may be included in such sunscreening formulations, the more significant additives are oils, fats, waxes, emulsifiers, surfactants, perfumes and preservatives. Artificial tanning agents such as dihydroxyacetone and conventional sunscreening agents such as P-aminobenzoic acid may also be employed in such formulations.

The amount of sunscreening agent incorporated into the substantive sunscreen compositions of the invention may vary greatly but is generally between about 1 and 15% by weight of the composition. One or more sunscreening agents may be incorporated into a single composition in which case, the combined concentration by weight of the composition is preferred in the range of about 1 to 15%.

Sunscreening compositions of the invention exhibit substantivity to skin to the extent that they are not removed by water, perspiration or simple abrasion but they are removable with soap and water. Compositions of the invention are also effective in absorbing ultraviolet radiation in the erythymal range. The preferred compositions are characterized by an ultraviolet absorption maxima in this range when measured after application to a proteinaceous surface such as pigskin gelatin. Certain compositions of the invention may have ultraviolet absorption maxima outside this range but this is not detrimental to their utility as sunscreens since they also exhibit a high degree of absorption in the erythemal range. The intensity with which compositions of the invention absorb radiation is a function of their concentration and molar extinction coefficient which must be at least 10,000.

The substantivity of the sunscreening agent and compositions of the invention and their ultraviolet absorption maxima are determined by applying the compositions in a normal manner to a pigskin gelatin substrate. The preparation of this "simulated skin" substrate is described in detail in the examples below. It was found that when active sunscreening agents of the invention were applied to the surface of the pigskin gelatin preparation, at least 50% of the amount applied remained adherent to the surface of the substrate after 1 hour immersion in water. The results of this test indicate that compositions of the invention have the ability to provide long-lasting protection against erythemal radiation even when the user perspires, swims or by any other manner comes in contact with water, yet the compositions are shown to be readily removed by soap and water during the normal act of bathing.

EXAMPLES

The following, non-limiting examples are illustrative of the preparation of the active ultraviolet absorbing compounds comprising the sunscreening compositions of the invention, the substantivity of these compounds to proteinaceous surfaces, and the incorporation of these compounds into pharmaceutically acceptable extending media.

In some of the examples the materials listed below are referred to by their trademarks or trade names. For reference purposes, the compositions of these materials are given below:

Carbopol ® 940 — Water soluble resin
   Chemical Structure — carboxyvinyl polymer
   Approx. Molecular Weight — 4,000,000
   Cosmetic thickening agent
Available from the B. F. Goodrich Chemical Co., 6100 Oak Tree Blvd., Cleveland, Ohio, 44131
DDI ® Brand Diisocyanate 1410 — Aliphatic diisocyanate
   Chemical Structure — OCN—D—NCO where D is a 36 carbon hydrocarbon radical
   Physical Form — Clear, amber, low viscosity syrup
   Molecular Weight — Approx. 600
   Equivalent Weight — Approx. 300
   NCO Content — 14%
   Chemical Reactivity — Reacts with materials containing active hydrogen atoms
Available from General Mills Co., 4620 W. 77th Street, Minneapolis, Minnesota 55413
Kind and Knox Gelatin 1312
Composition: Gelatin obtained from porkskin by the acid process.
General Characteristics: Off-white, granular solid
Basic Properties:

| | |
|---|---|
| pH | 5.1–5.8 |
| Ash | 0.2% max. |
| Moisture | 12% max. |
| Copper | 5 p.p.m. max. |
| Iron | 20 p.p.m. max. |
| Isoionic point | 9.0–9.3 |
| Nitrate (as NO$_2$) | 10 p.p.m. max. |
| Viscosity (6.66% soln. at 60° C.) | 50–60 mp |
| Particle Size Distribution: | |
| Retained by 6 mesh | Less than 2% |
| Retained by 20 mesh | 58–80% |
| Retained by 40 mesh | 80–95% |
| Retained by 60 mesh | 94–100% |
| Retained by 100 mesh | 98–100% |
| Passed by 100 mesh | Less than 2% |

Hystrene ® 3695 — Essentially a dicarboxylic acid produced by the polymerization of C-18 fatty acids.
   Physical Form — Light-yellow, viscous syrup
   Composition
      υ1% monobasic acid
      υ95% dibasic acid
      υ4% tribasic acid
   Equivalent Weight — 283–289
   Further Information — Humko Products Chemical Division, Technical Bulletin SAI-4,6, and 8.
Available from Humko Products Chemical Division, White Station Tower, Memphis, Tennessee, 38101
Empol ® 1056A Polybasic Acid — Polymerized fatty acid, aliphatic polycarboxylic acid.
   Composition
      υ1% monobasic acid
      υ59% dibasic acid
      υ40% polybasic acid
   Estimated Carboxyl Functionality — 2.65–2.75
   Acid Value — 188–192
   Additional Data — Available from Emery Tech. Bulletin No. 204, Emery Industries, Inc., Carew Tower, Cincinnati, Ohio, 45202

EXAMPLE 1

Preparation of:

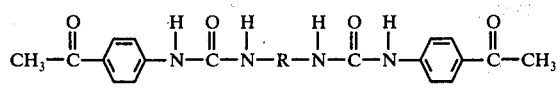

where R is the aliphatic portion of General Mills Brand DDI® 1410

Thirty five grams (0.10 equiv.) of General Mills Brand DDI® 1410, 13.5 g (0.100 equiv.) of 4-aminoacetophenone, 100 ml of toluene and 0.10 g of stannous octoate were placed into a 250 ml round bottom flask equipped with a magnetic stirrer and a reflux condenser. The homogeneous solution was refluxed for four hours at which time the reaction was found to be complete by infrared spectral analysis which indicated the absence of isocyanate absorption at 2300 cm$^{-1}$ and the presence of a strong urea carbonyl band at 1660 cm$^{-1}$. The solution was cooled and the solvent was removed by evaporation in vacuo to give a quantitative yield of pale amber wax having an absorption maxima at 302 nm and a molar extinction coefficient (Epsilon value) of 55,000.

EXAMPLE 2

Preparation of:

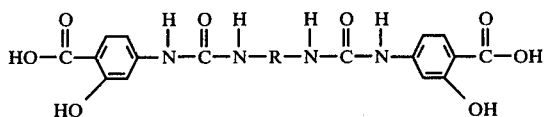

where R is the aliphatic portion of General Mills Brand DDI® 1410

Into a 250 ml round bottom flask equipped with a magnetic stirrer and condenser were placed 61.0 g (0.20 equiv.) of General Mills Brand DDI® 1410, 31.2 g (0.20 equiv.) of 4-aminosalicylic acid, 150 ml of tetrahydrofuran, and 0.20 g of dibutyltindilaureate. The heterogeneous solution was refluxed and became homogeneous as the reaction proceeded. After refluxing for 3 hours, infrared spectral analysis indicated that the reaction was complete by the absence of an isocyanate band at 2300 cm$^{-1}$ and the presence of a strong urea carbonyl band at 1650 cm$^{-1}$. The solvent was removed by evaporation in vacuo to give a quantitative yield of white powder which was soluble in ethanol and isopropanol. An ultraviolet spectrum obtained in ethanol solvent showed this product to have an absorption maximum at 303 nm with an Epsilon value of 22,000.

EXAMPLE 3

Preparation of:

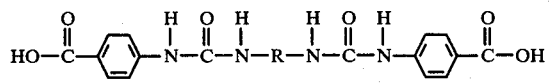

where R is the aliphatic portion of General Mills Brand DDI® 1410

Example 2 was repeated using 27.45 g (0.20 equiv.) of 4-aminobenzoic acid as the U.V. absorbing coreactant in place of 4-aminosalicyclic acid. The reaction was allowed to proceed at ambient temperature until infrared spectral analysis indicated that the reaction was complete by the absence of an isocyanate band at 2300 cm$^{-1}$ and the presence of a urea carbonyl band at 1650 cm$^{-1}$. The solvent was removed by evaporation in vacuo to give a quantitative yield of yellow powder. An ultraviolet spectrum obtained in ethanol solvent showed this product to have an absorption maximum at 272 nm with an Epsilon value of 41,000.

EXAMPLE 4

Preparation of:

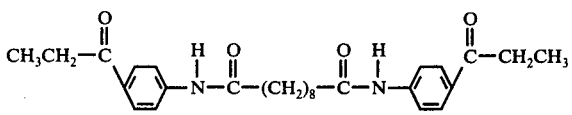

Twelve grams (0.10 equiv.) of sebacoyl chloride, 14.0 g (0.10 mole) of 4-aminopropiophenone, 16 g of sodium bicarbonate, and 120 ml of benzene were placed into a 250 ml round bottom flask equipped with a reflux condenser and magnetic stirrer. The mixture was refluxed for about 6 hours, the solvent was removed by evaporation in vacuo, the product was washed with water and dried to give a near-quantitative yield of white product. An infrared spectral analysis of the product showed complete loss of an acid chloride band at 1750 cm$^{-1}$ and the presence of a strong amide band at 1650 cm$^{-1}$. The product had an ultraviolet absorption maximum at 292 nm with an Epsilon value of 48,000.

EXAMPLE 5

Preparation of:

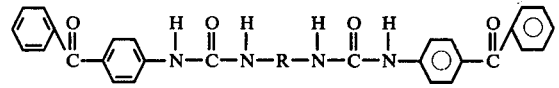

where R is the aliphatic portion of General Mills Brand DDI® 1410

Into a 100 ml round bottom flask equipped with a magnetic stirrer and a reflux condenser were placed 15.25 g (0.050 equiv.) of General Mills Brand DDI® 1410, 9.19 g (0.050 equiv.) of 4-aminobenzophenone, 50 ml of tetrahydrofuran, and 0.25 g of dibutyltindilaureate. The contents were refluxed for 2 hours at which time infrared spectral analysis indicated that the reaction was complete by the absence of an isocyanate band at 2300 cm$^{-1}$ and the presence of a urea carbonyl band at 1650 cm$^{-1}$. The solvent was removed by evaporation in vacuo to yield 23.6 g (94%) of a golden-yellow, viscous liquid. An ultraviolet spectrum obtained in ethanol solvent indicated this product absorption maximum at 312 nm with an Epsilon value of 35,000.

EXAMPLE 6

Preparation of:

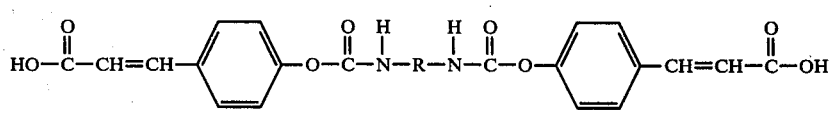

where R is the aliphatic portion of General Mills Brand DDI ® 1410

Example 5 was repeated using 8.20 g (0.05 equiv.) of 4-hydroxycinnamic acid as the ultraviolet absorbing coreactant in place of 4-aminobenzophenone. A golden-colored viscous liquid product was obtained in theoretical yield. An ultraviolet spectrum determined in 2-propanol solvent indicated that this product had an absorption maximum at 280 nm with an Epsilon of 28,500.

EXAMPLE 7

Preparation of:

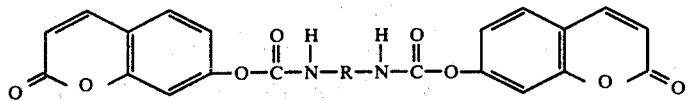

where R is the aliphatic portion of General Mills Brand DDI ® 1410.

Example 6 was repeated using an equimolar quantity of 7-hydroxycoumarin as the ultraviolet absorbing coreactant in place of 4-hydroxycinnamic acid. A theoretical yield of a pale yellow solid product was obtained which was soluble in ethanol and isopropanol. An ultraviolet spectrum determined in ethanol solvent indicated that this product had an absorption maximum at 330 nm with an Epsilon value of 26,500.

EXAMPLE 8

Preparation of:

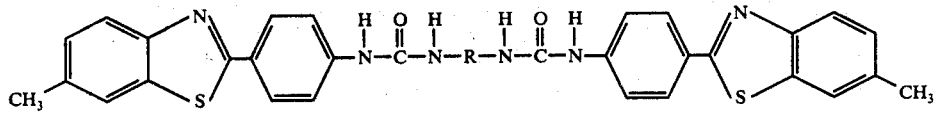

where R is the aliphatic portion of General Mills Brand DDI ® 1410

Example 6 was repeated using an equimolar quantity of 2-(4-aminophenyl)-6-methyl benzothiazole as the ultraviolet absorbing coreactant in place of 7-hydroxycoumarin. A brown powder was isolated in near quantitative yield which was moderately soluble in ethanol and isopropanol. The ultraviolet spectrum determined in 1-methyl pyrrolidone solvent indicated that this product had an absorption maximum at 337 nm with an Epsilon value of 77,000.

EXAMPLE 9

Preparation of:

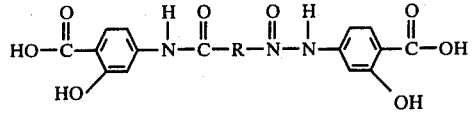

where R is the aliphatic portion of Humko Brand Hystrene ® 3695 dimer acid.

One-tenth equivalent weight of Humko Brand Hystrene ® 3695 dimer acid was stirred at room temperature with one-tenth mole of phosphorous trichloride. After about 3 hours, infrared spectral analysis of the solution indicated nearly complete conversion of the acid to the acid chloride by the presence of a strong acid chloride carbonyl band at 1780 cm$^{-1}$. The excess phosphorous trichloride was removed at reduced pressure and the product used without further preparation for the next step.

Into a 250 ml round bottom flask equipped with a magnetic stirrer and reflux condenser were placed 32.5 g (0.10 equiv.) of dimer acid chloride prepared above, 75 ml of 2-propanone and 8.5 g (0.11 mole) of pyridine. To this mixture was added 15.4 g (0.10) of 4-aminosalicylic acid and the entire mixture was refluxed for 3 hours. The product was precipitated into an excess of water, washed with water, and dried in vacuo to give a white solid in near quantitative yield. The ultraviolet spectrum as determined in ethanol indicated that this product had an absorption maximum at 303 nm with an Epsilon value of 13,000.

EXAMPLE 10

Preparation of:

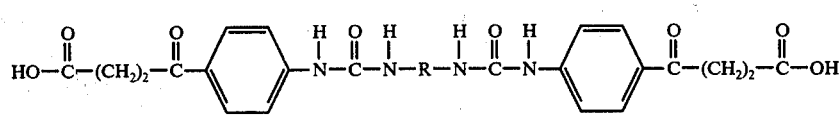

where R is the aliphatic portion of General Mills Brand DDI ® 1410.

Example 8 is repeated using 8.60 g (0.050 equiv.) of 3-(4-aminobenzoyl) propionic acid as the ultraviolet absorbing coreactant in place of 2-(4-aminophenyl)-6-methyl-benzothiazole. The pale brown reaction product obtained had an ultraviolet absorption maximum in ethanol solvent at 295 nm with an Epsilon value of 45,000.

EXAMPLE 11

Preparation of:

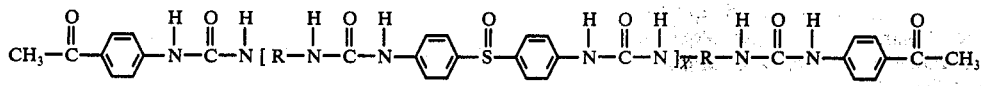

where R is the aliphatic portion of General Mills Brand DDI® 1410, X = approx. 14.

Into a 100 ml round bottom flask equipped with a magnetic stirrer and reflux condenser were placed 7.00 g (0.020 equiv.) of General Mills Brand DDI®, 2.18 g (0.0175 equiv.) of 4,4'-sulfonyldianiline, 0.350 g (0.0025 equiv.) of 4-aminoacetophenone, 50 ml of tetrahydrofuran, and 0.1 g of stannous octoate. The mixture was heated at reflux temperature until infrared spectral analysis indicated that the reaction was complete by the absence of the isocyanate band at 2300 cm$^{-1}$. The solvent was removed by evaporation in vacuo to give a quantitative yield of a pale yellow glass product whose ultraviolet spectrum in tetrahydrofuran solvent had an absorption maximum at 292 nm with an Epsilon value of 550,000.

EXAMPLE 12

Preparation of:

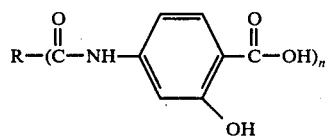

where R = aliphatic radical of Empol® 1056A polybasic acid n = 2.65 to 2.75

One equivalent weight of Emery Empol® 1056A polybasic acid was stirred at room temperature with 1 mole of phosphorous trichloride. After about 3 hours, infrared spectral analysis of the solution indicated nearly complete conversion of the acid to the acid chloride by the presence of a strong acid chloride carbonyl band at 1780 cm$^{-1}$. The excess phosphorous trichloride was removed at reduced pressure and the product used without further purification for the next step.

Into a 600 ml beaker equipped magnetic stirrer were placed 7.5 g (0.05 mole) of 4-aminosalicylic acid, 7.5 g (0.05 mole) of potassium carbonate and 70 ml of distilled water. To this rapidly stirred solution was added 16.5 g (0.05 equiv.) of Empol® 1056A acid chloride prepared above and dissolved in 60 ml of methyl ethyl ketone. The mixture was stirred for about 20 minutes, acidified with concentrated hydrochloric acid and the organic phase was separated from the water phase. The organic phase was washed once with water and the solvent was removed by evaporation in vacuo to give 24.4 g of a pale yellow solid product which had an ultraviolet absorption maxima in ethanol solvent at 303 nm with an Epsilon of 32,000 as determined in ethanol.

EXAMPLE 13

This example illustrates the preparation of a typical sunscreening composition containing one of the novel, substantive sunscreen agents of the invention. The gel formulation of this example was prepared according to the procedure described by B. F. Goodrich Chemical Company, Carbopol Resins Newsletter #3, employing the product of Example 2 as the sunscreening agent. The composition contained the ingredients given below and was prepared by adding the homogeneous Part B to the homogeneous Part A with agitation followed by the addition of Part C.

| | | Parts |
|---|---|---|
| Part A | | |
| | Product of Example 2 | 5.0 |
| | Ethanol 190 Proof | 55.0 |
| | Carbopol® 940 | 1.0 |
| Part B | | |
| | Water | 30.0 |
| | Allantoin | 0.2 |
| Part C | | |
| | Diisopropanol amine | 0.50 |
| | Water | 8.3 |

This sunscreening composition was found to be pleasant to apply and left an indiscernible coating on the user's skin.

EXAMPLE 14

Example 13 was repeated except that in place of the product of Example 2, 5 parts by weight of the product of Example 1 was employed as the sunscreening agent in the formulation. This formulation likewise had a pleasant feel and left an indiscernible film on the user's skin.

EXAMPLE 15

This example illustrates the preparation of typical sunscreening composition of the invention in the form of an aqueous emulsion of the oil-in-water type containing the sunscreening agent prepared in Example 1. The composition contained the ingredients given below and was prepared by the addition of Part A to Part B with rapid agitation whereupon the desired oil-in-water emulsion was obtained.

| | | Parts by Weight |
|---|---|---|
| Part A | | |
| | Sunscreening agent of Example 1 | 3.0 |
| | Isopropyl myristate | 12.0 |
| | Isopropanol | 3.0 |
| | Stearic acid | 1.0 |
| | Cetyl alcohol | 0.5 |
| Part B | | |
| | Triethanolamine | 1.0 |
| | Carbopol® 940 | 0.2 |
| | Water | 79.3 |

EXAMPLE 16

This example illustrates the preparation of a thick sunscreening composition in a cream form. Example 15 was repeated except that 5 parts by weight of the sunscreening agent of Example 1 was used as well as 2 parts by weight each of stearic acid and triethanolamine. The thick cream produced was easy to apply and left an indiscernible film on the user's skin.

EXAMPLE 17

The controlled evaluation of the substantivity and sunscreening properties of the substantive sunscreen agents of this invention was carried out by using a pigskin gelatin substrate. This substrate provides a proteinaceous surface used as a model for human skin. The pigskin gelatin substrates were prepared using the following ingredients:

|  |  |
|---|---|
| Pig-skin gelatin (Kind and Knox 1312) | 300 g |
| 15% Saponin | 60 ml |
| Sorbitol - H₂O (1:2) | 30 ml |
| 3.7% Formaldehyde | 22 ml |
| Water (Deionized) | 5408 ml |
| 1% Thymol | 30 ml |
| Total Weight = | 5850 g |

A liquid composition was prepared by mixing together the above ingredients. This liquid composition was single-slot coated on both sides of a cellulose triacetate film (5 mil thickness) under the following conditions:

Flow rate — 190 ml/min.
Coating speed — 16 g/min.
Coating width — 8 3/4 in.

The coating was air dried and the final coating (on one side) contained 104 mg. gelatin per square decimeter.

The products of Examples 1-3, 6, and 8-11 were each applied as a 5% solution in alcohol to a pig-skin gelatin substrate prepared by the above method. The sunscreening compositions of Examples 13 and 14 were each applied without dilution to the gelatin substrate. The ultraviolet absorption maxima in the range of 280 nm to 330 nm were then determined spectroscopically for each material. The initial value obtained for each material was directly proportional to the amount of sunscreening product present on the substrate.

Each treated substrate was then challenged by immersion for a period of hours in fresh water and in some instances salt water. After water challenge, the ultraviolet absorption maxima in the range 280 nm and 330 nm were again determined for each material. In this way the percent of each product remaining after challenge was determined. Such a determination provides a measure of substantivity to a particular proteinaceous surface. After challenge with water, and determination of the percent of product remaining, substrates coated with products of Examples 2, 10 and 14 were additionally subjected to an 1 hour soak in detergent solution to determine the soap-removability of these materials were completely removed by detergent soak.

Results obtained from this test are presented in the following table:

Effect of Water Challenge on Sunscreening Agents of the Invention

| Product of Example | Absorption Maximum, nm | Hours Challenge by Fresh of Salt Water* or 1% Detergent Solution** | Percent Remaining |
|---|---|---|---|
| 1 | 303 | 1 Fresh | 94 |
| 2 | 297 | 2 Fresh | 81 |
|  |  | 1 Detergent | 0 |
| 3 | 289 | 1 Fresh | 86 |
| 6 | 297 | 18 Fresh | 70 |
| 8 | 313 | 18 Fresh | 95 |
| 9 | 313 | 2 Fresh | 80 |
| 10 | 298 | 18 Fresh | 86 |
|  |  | 1 Detergent | 0 |
| 11 | 294 | 18 Fresh | 90 |
|  |  | 2 Salt | 90 |
| 13 | 300 | 5 Fresh | 81 |
| 14 | 310 | 16 Fresh | 50 |
|  |  | 1 Detergent | 0 |

*Prepared from "H.W. Marine Mix" distributed by Hawaiian Imports, Town and Country Village, Houston, Texas 77024
**Alconox R, wetting agent and detergent obtained from Alconox, Inc., New York, NY 10003

The above data indicate that the sunscreening agents and compositions of this invention have outstanding substantivity toward proteineous surfaces. The data further indicate that the materials are readily removable by detergent solutions.

We claim:

1. In a sunscreening composition comprising a pharmaceutical extending medium and an effective sunscreening amount of a dermally non-irritating, ultraviolet light-absorbing compound, the improvement wherein the dermally non-irritating, ultraviolet light-absorbing compound is a substantive compound of the formula $$(XE)_n—R—(AY)_{n^1}$$

Wherein R is the aliphatic portion of polymerized 18-carbon fatty acids and contains 34, 51, 68, 85 or 102 carbon atoms;

A and E are independently

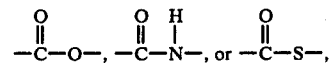

X and Y are aromatic, ultraviolet light absorbing moieties characterized by ultraviolet light absorption maxima in the range of 280 nm to about 360 nm, and when $n + n^1$ is greater than 2, Y may be hydrogen or an alkyl radical containing 1 to 6 carbon atoms; $n$ and $n^1$ are independently integers from 1 to 6 designating different or the same (XE)— and —(AY) respectively, except $n + n^1$ must equal 2-6.

2. A composition according to claim 1 wherein A and E are independently

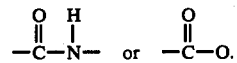

3. A composition according to claim 2 wherein X and Y are independently

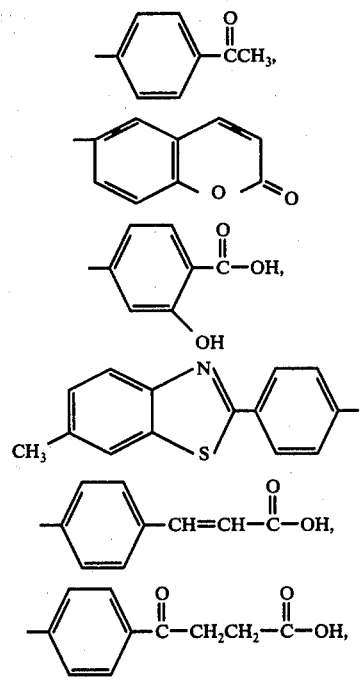

-continued
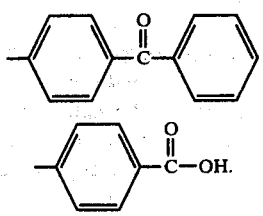
4. The composition according to claim 2 wherein A and E are
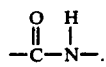
5. The composition according to claim 3 wherein the compound is
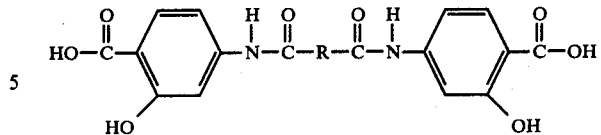
and R contains 34 carbon atoms.
6. The composition according to claim 3 wherein the compound is
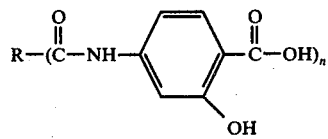
wherein $n$ is 2.65 to 2.75.
* * * * *